US00PP08835P

United States Patent [19]

Schuhman

[11] Patent Number: Plant 8,835

[45] Date of Patent: Jul. 12, 1994

[54] COLEUS PLANT NAMED HEIDI

[76] Inventor: Wolfgang W. Schuhman, 7441 Curtiss Ave., Sarasota, Fla. 34231

[21] Appl. No.: 25,446

[22] Filed: Mar. 2, 1993

[51] Int. Cl.[5] ..... A01H 5/00

[52] U.S. Cl. ..... Plt./88.1

[58] Field of Search ..... Plt. 68.1, 88.1

[56] References Cited

PUBLICATIONS

Anon., "Coleus" 1987 Thompson and Morgan Seed catalog, p. 63.

Anon., "Coleus Flower Seed" Ball '78 Seed Catalog, pp. 16–17.

Anon., "Coleus" 1984 Burpee Gardens Seed Catalog, p. 26.

*Primary Examiner*—James R. Feyrer

*Attorney, Agent, or Firm*—Gifford, Groh, Sprinkle, Patmore and Anderson

[57] ABSTRACT

A new distinct variety of coleus, characterized by its compact, large, and symmetrically domed shape and its deep maroon color.

2 Drawing Sheets

FIELD OF THE INVENTION

This invention relates to a coleus plant, and, more particularly this invention relates to a new hearty variety of coleus which grows to a large, distinctive dome shape, atypical of unpruned coleus plants, and which retains a distinctive new vivid velvety maroon color not approached by any known coleus variety, which color is retained even under full hot sunlight.

BACKGROUND OF THE INVENTION

Although the coleus is a perennial of the nettle family, many gardeners treat it as a temporary foliage plant, to be enjoyed in full coloration but to be discarded when past its prime. This is due in part to the tendency of normal strains of coleus to fade in color under bright light even under adequate moisture level and other cultural conditions even though deeper shades are retained under shade and partial shade conditions. Also the coleus is generally easy to grow from new cuttings, making it easy to treat as a temporary or seasonal planting. Usually growth of the coleus plant is obtained by pinching.

While the coleus grows in a number of colors and shades varying from yellows, reds, oranges, greens and browns with numerous variegations which have been developed such as Pink Rainbow and Yellow Bedder there are no known varieties that approach the deep solid coloration of the coleus plant of the present variety.

Unpruned and untrained coleus plants of previous varieties do not generally grow to the large, symmetrically domed shape of the coleus plant of the present variety.

DETAILED DESCRIPTION OF THE DRAWING

DETAILED DESCRIPTION

Figure 1:
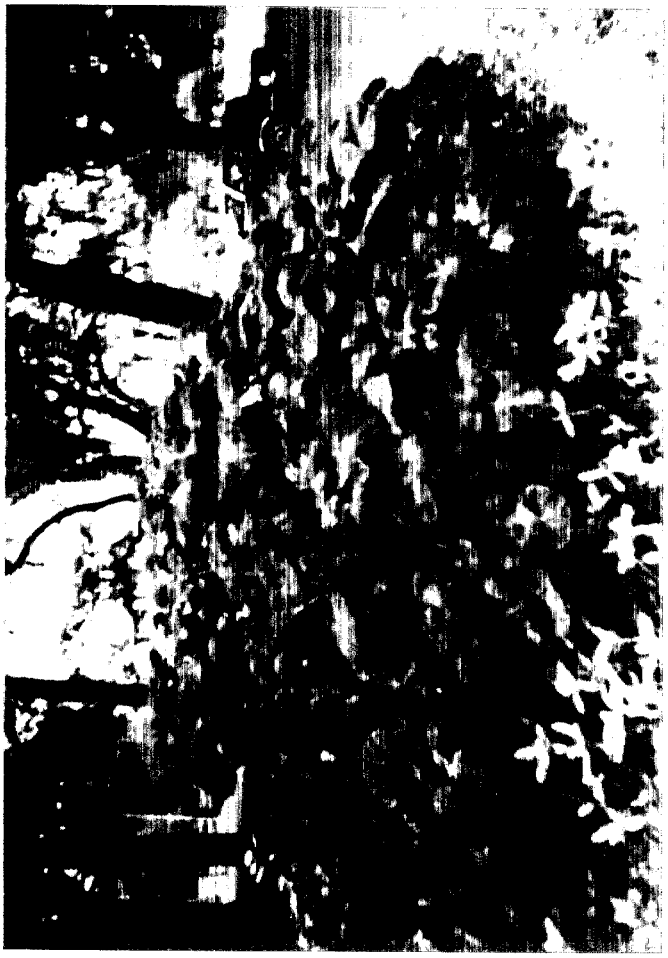
FIG. 1 depicts a mature specimen of the claimed plant in an outdoor planting in full sun, and depicts the mounding habit of 'Heidi' as well as the deep color of the plant and the unusually dense canopy of this plant when so grown.
Figure 2:
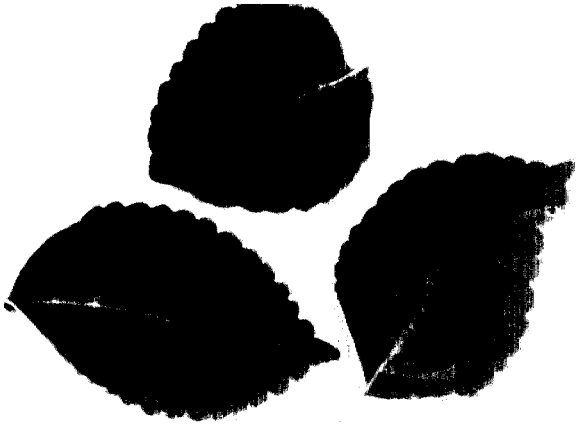
FIG. 2 shows the top surface of three individual leaves of the plant and illustrates the leaf shape, margin characteristics, petiole, venation and color of typical leaves from the plant; and, FIG. 3 shows the underside of a typical leaf from the plant to show the venation, texture and coloration of the underside of the leaves and the leaf petiole.
Figure 3:
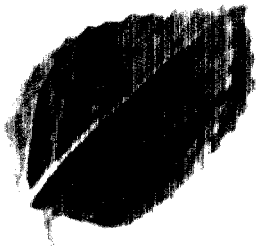

The present variety of coleus was originally taken as a natural mutant stem of dark maroon color from a common coleus plant of conventional coloration growing in the summer season in Sarasota, Fla. The plant from which a cutting was taken was one plant observed in a large group of about 500 coleus plants grown in 6" pots, all of same unnamed coleus variety. This parent plant had a color of a green, brown and red mixture spotted on the leaf surface.

Started with a single rooted cutting, the plant has been asexually propagated by successive cuttings, all having the characteristic deep maroon color.

The initial cutting and successive cuttings of the new variety have been grown side by side in full Sarasota, Fla. sunlight. The following observations are made of the parent and the new variety, Heidi as they are grown, watered and fed under the same conditions. Comparisons are made at the same stage of growth. With identical treatment such observations clearly indicate genetic change and not any attempt to effect the changes by acclimatizing the Heidi specimen by different conditions than those to which the parent plant is exposed.

The stems are yellow green (Royal Horticultural Society Colour Chart yellow green 144B), 0.4 mm diameter, with a maximum internode length of 4 cm. In cross section the stems are square. The internoded areas are splashed with flecks of red, purple (R.H.S. red purple 59B). The leaves are opposite with leaf blades obovate, with scalloped margins of 0.5 cm lobes. Leaf blade is up to 8 cm long and 6.5 cm wide. Leaf color is a dark maroon (darker than RHS 59A) when grown in full sun. The petiole is round with a flattened abaxial surface, up to 3 cm long and a diameter of 2.5 mm. Petiole color is slightly lighter than the stem color (RHS 144B). The axillary buds are predominant even, and, generally, two small (1.4 cm long and 0.5 cm wide) leaves are visible at each axil. The upper basal surface of the leaf may exhibit a small reddish purple (RHS 60C) area up to 1.5 cm long and wide and is more pronounced when plants are grown in areas with less than full sun. The lower leaf surface is a lighter shade of red purple (RHS red purple 61A), with prominent green main and secondary pinnate venation (RHS yellow green 145B). The intervenial areas near the lower base and margins are intermixed with light green (RHS yellow green 145B) and red purple (RHS red purple 61A).

The plant has been propagated asexually by stem cuttings and have been true to form and color after two (2) years of propagation. The inflorescence is a typical raceme with pale blue flowers (RHS blue green 133D) and infrequently produce seed. Seed collected, planted and evaluated upon germination have produced only plants with variegated green and yellow leaves with occasional brown center. No dark maroon-leaf seedlings have been found among these seedlings.

The plant develops new shoots from the base and side shoots with no pinching, being stronger than any regular pinched coleus.

The plant of this application is of exceptionally high vigor, strongly basally dominant and, in branching, readily breaks basally as well as progressively at axillary buds along the main and secondary stems without chemical induction or pinching. This plant thrives when grown under normal outdoor, full sunlight conditions under which many other coleus plants are not adapted to survive even if carefully exposed to conditions which would have hardened them to such conditions.

The plant of this invention differs in habit from those typical of most available coleus plants which are market available, by forming a plant with a denser canopy of large, healthy leaves which are imbricated in their presentatiuon, nearly concealing the stems of the plant. In habit, with no pruning, this plant attains a symmetrical, domed shape which will result in a plant which is more than twice as wide as tall, one typical specimen being 55" wide and only 18" tall after being grown in full sun for one year. Such growth is inconsistent with that of the typical plant of the species or market class which would not normally have survived under such conditions.

The coleus of the present variety is rather slow to flower, producing blossoms only once in five months. The blossoms are typical of the market class.

Test plants planted in poor soil and grown in shade or partial shade exhibit a very dark maroon color and maintain a satisfactory but not rapid growth rate.

The most dominant features of the coleus of the present variety are its deep maroon color which persists in strong sunlight without fading and the compact, rather large domed shape that it grows into.

Parentage: Mutant cutting of ordinary coleus.
Propagation: Cutting.
Plant:
*Form.*—Basally dominant.
*Growth.*—Vigorous and hearty under all light conditions, from shade, partial shade to full sunlight.
*Blooming habits.*—Slow, once in 5 months.
Height: 6" to 2'.
Spread: 3' to 5'.
Shape: Large, symmetrically domed.
Color: Deep vivid velvety maroon.
Name: Heidi.

I claim:

1. A new and distinct variety of coleus plant substantially as herein shown and described, characterized by its compact, large, and symmetrically domed shape and its deep maroon color.

* * * * *

UNITED STATES PATENT AND TRADEMARK OFFICE

CERTIFICATE OF CORRECTION

PATENT NO. : Plant 8,835
DATED : July 12, 1994
INVENTOR(S) : Wolfgang W. Schuhmann It is certified that error appears in the above-indentified patent and that said Letters Patent is hereby corrected as shown below:

On the title page, under item [19] and item [76], change "Schuhman" to —Schuhmann—.

Column 3, lines 34 and 35, change "presentatiuon" to --presentation--.

Signed and Sealed this
Twenty-first Day of March, 1995

*Attest:*

*Attesting Officer*

BRUCE LEHMAN

*Commissioner of Patents and Trademarks*